(12) United States Patent
Utsumi et al.

(10) Patent No.: US 11,852,638 B2
(45) Date of Patent: Dec. 26, 2023

(54) CALCIUM ION CONCENTRATION MEASURING DEVICE

(71) Applicant: HORIBA Advanced Techno, Co., Ltd., Kyoto (JP)

(72) Inventors: Rika Utsumi, Kyoto (JP); Manabu Shibata, Kyoto (JP)

(73) Assignee: HORIBA ADVANCED TECHNO, CO., LTD., Kyoto (JP)

( * ) Notice: Subject to any disclaimer, the term of this patent is extended or adjusted under 35 U.S.C. 154(b) by 534 days.

(21) Appl. No.: 17/271,763

(22) PCT Filed: Aug. 2, 2019

(86) PCT No.: PCT/JP2019/030519
§ 371 (c)(1),
(2) Date: Feb. 26, 2021

(87) PCT Pub. No.: WO2020/044958
PCT Pub. Date: Mar. 5, 2020

(65) Prior Publication Data
US 2022/0026450 A1    Jan. 27, 2022

(30) Foreign Application Priority Data
Aug. 28, 2018    (JP) .................. 2018-159798

(51) Int. Cl.
*G01N 33/84* (2006.01)
*G01N 33/49* (2006.01)
*B01L 3/00* (2006.01)

(52) U.S. Cl.
CPC ............ *G01N 33/84* (2013.01); *B01L 3/5023* (2013.01); *B01L 13/02* (2019.08); *B01L 2300/046* (2013.01); *B01L 2300/069* (2013.01)

(58) Field of Classification Search
CPC ........ G01N 33/84; G01N 33/49; B01L 13/02; B01L 3/5023
(Continued)

(56) References Cited

U.S. PATENT DOCUMENTS 4,618,587 A * 10/1986 Premoli ................. H02K 19/34
436/16
4,713,165 A * 12/1987 Conover ................ C12Q 1/001
204/411
(Continued)

FOREIGN PATENT DOCUMENTS

CN        103185740 A     7/2013
CN        103185741 A     7/2013
(Continued)

OTHER PUBLICATIONS

Gyurcsanyi, R. E. et al, Talanta 2004, 63, 88-99. (Year: 2004).*
(Continued)

*Primary Examiner* — Arlen Soderquist
(74) *Attorney, Agent, or Firm* — Alleman Hall Creasman & Tuttle LLP

(57) ABSTRACT

The present claimed invention provides a calcium ion concentration measuring device that can measure a concentration of a calcium ion in blood of a domestic animal with high accuracy without being affected by temperature on the spot where the blood is collected. The calcium ion concentration measuring device is a portable one for measuring the concentration of the calcium ion in the blood of the domestic animal, and comprises a responsive membrane that selectively reacts with the calcium ion, an internal liquid stored in a space separated from the outside by the responsive membrane, and an internal electrode arranged to be in contact with the internal liquid, and the isothermal intersection point of the internal liquid is set within a range of the (Continued)

concentration of the calcium ion contained in the blood of the domestic animal.

10 Claims, 8 Drawing Sheets

(58) Field of Classification Search
USPC .......................................................... 436/79
See application file for complete search history.

(56) References Cited

U.S. PATENT DOCUMENTS

| | | | | |
|---|---|---|---|---|
| 5,013,666 | A * | 5/1991 | Chiang ................. | G01N 33/84 436/15 |
| 5,023,186 | A * | 6/1991 | Herring .............. | G01N 27/4165 436/8 |
| 5,472,590 | A * | 12/1995 | Yamashita ......... | G01N 27/3335 257/253 |
| 5,863,972 | A * | 1/1999 | Beckelmann ...... | G01N 27/3335 524/588 |
| 2013/0168247 | A1* | 7/2013 | Iwamoto .............. | G01N 27/333 204/417 |

FOREIGN PATENT DOCUMENTS

| | | |
|---|---|---|
| CN | 103675055 A | 3/2014 |
| CN | 103728356 A | 4/2014 |
| CN | 105353018 A | 2/2016 |
| CN | 107922964 A | 4/2018 |
| EP | 3321372 A1 | 5/2018 |
| IN | 106338540 A | 1/2017 |
| JP | S5767856 A | 4/1982 |
| JP | H02087055 A1 | 3/1990 |
| JP | H07325063 A | 12/1995 |
| JP | 2007024544 A | 2/2007 |
| JP | 2013137216 A | 7/2013 |
| WO | 2014127379 A1 | 8/2014 |

OTHER PUBLICATIONS

Lindner, E. et al, Journal of Solid State Electrochemistry 2009, 13, 51-68. (Year: 2009).*
European Patent Office, Extended European Search Report Issued in Application No. 19854701.0, dated Apr. 8, 2022, Germany, 9 pages.
China National Intellectual Property Administration, Office action issued in Chinese Application No. 201980056716.4, dated Feb. 22, 2023, 20 pages.
Japan Patent Office, Notice of Reasons for Refusal issued in Japanese Application No. 2020-540192, dated Jan. 5, 2023, 8 pages.
Abaxis Inc. VetScan i-STAT 1 Handheld Analyzer Brochure, Available Online at https://www.equipmentoutreach.com/wp-content/uploads/2016/07/i-STAT-Brochure-887-0002-Rev.-G.pdf, Available as Early as 2015, Retrieved on Sep. 30, 2019, 6 pages.
Horiba Ltd. B-700 series LAQUAtwin Compact Water Quality Meter Catalog, Available Online at http://www.nissoden.co.jp/assets/LAQUAtwin.pdf, Available as Early as Aug. 2017, Retrieved on Sep. 30, 2019, 12 pages.
Horiba Advanced Techno Co. Ltd. Instruction Manual of Compact Water Quality Meter of LAQUAtwin-Ca-11, Available Online at https://www.specmeters.com/assets/1/22/2450L_LAQUA_Twin_Ca_Meter_(Horiba,_2017).pdf, Available as Early as Mar. 2017, Retrieved Oct. 1, 2019, 2 pages.
ISA Japan Patent Office, International Search Report Issued in Application No. PCT/JP2019/030519, dated Oct. 21, 2019, 3 pages.
Neves, R.C. et al., "Method comparison and validation of a prototype device for measurement of ionized calcium concentrations cow-side against a point-of-care instrument and a benchtop blood-gas analyzer reference method," Journal of Dairy Science, vol. 101, No. 2, Dec. 13, 2017, 10 pages.
Umezawa, Y., "Ion-Selective Electrode," Journal of The Society of Instrument and Control Engineers, vol. 25, No. 11, 1986, 4 pages.
Vasconcelos, M. T. S. D. et al., "Evaluation of the Temperature Influence on the Response Characteristics of Poly (vinyl chloride) Membrane Calcium Ion-selective Electrodes With an Internal Reference or Applied to an Electrically Conductive Silver-Epoxy Support," Analyst, vol. 115, Feb. 1990, 8 pages.

* cited by examiner

| TEMPERATURE | SENSOR | MEASURED VALUE (mM) | DIFFERENCE BETWEEN ABL AND MEASURED VALUE(mM) | AVERAGE (mM) | | AVERAGE TIME UNTIL POTENTIAL IS STABILIZED (sec) |
|---|---|---|---|---|---|---|
| | | | | MEASURED VALUE | DIFFERENCE BETWEEN ABL AND MEASURED VALUE | |
| 37°C | THIS INVENTION | 1.06<br>1.02<br>1.02 | -0.21<br>-0.25<br>-0.25 | 1.04 | -0.23 | 18.30 |
| | CONVENTIONAL | 1.08<br>1.07<br>1.08 | -0.19<br>-0.20<br>-0.19 | 1.08 | -0.19 | 23.00 |
| 25°C | THIS INVENTION | 1.21<br>1.20<br>1.21 | -0.19<br>-0.20<br>-0.19 | 1.21 | -0.19 | 8.70 |
| | CONVENTIONAL | 1.26<br>1.24<br>1.21 | -0.14<br>-0.16<br>-0.19 | 1.23 | -0.17 | 10.02 |
| 5°C | THIS INVENTION | 1.55<br>1.58<br>1.64 | 0.27<br>0.30<br>0.36 | 1.59 | 0.31 | 8.00 |
| | CONVENTIONAL | 1.79<br>1.85<br>1.81 | 0.51<br>0.57<br>0.53 | 1.82 | 0.54 | 6.80 |

FIG. 6

| MEASURED DATE | SENSOR No. | MEASURED VALUE (mM) | DIFFERENCE BETWEEN ABL AND MEASURED VALUE(mM) | AVERAGE(mM) | |
|---|---|---|---|---|---|
| | | | | MEASURED VALUE | DIFFERENCE BETWEEN ABL AND MEASURED VALUE |
| JANUARY 9 | #1 | 1.22 | -0.03 | 1.19 | -0.06 |
| | | 1.19 | -0.06 | | |
| | | 1.20 | -0.05 | | |
| | #2 | 1.17 | -0.08 | | |
| | | 1.20 | -0.05 | | |
| | | 1.18 | -0.07 | | |
| JANUARY 17 | #1 | 1.17 | -0.09 | 1.18 | -0.08 |
| | | 1.17 | -0.09 | | |
| | | 1.20 | -0.06 | | |
| | #2 | 1.20 | -0.06 | | |
| | | 1.15 | -0.11 | | |
| | | 1.18 | -0.08 | | |
| JANUARY 24 | #1 | 0.86 | -0.08 | 0.83 | -0.11 |
| | | 0.84 | -0.10 | | |
| | | 0.80 | -0.14 | | |
| | #2 | 0.85 | -0.09 | | |
| | | 0.84 | -0.10 | | |
| | | 0.81 | -0.13 | | |
| JANUARY 31 | #1 | 1.13 | -0.12 | 1.19 | -0.06 |
| | | 1.19 | -0.06 | | |
| | | 1.22 | -0.03 | | |
| | #2 | 1.13 | -0.12 | | |
| | | 1.21 | -0.04 | | |
| | | 1.25 | 0.00 | | |
| FEBRUARY 7 | #1 | 1.04 | -0.16 | 1.14 | -0.06 |
| | | 1.19 | -0.01 | | |
| | | 1.16 | -0.04 | | |
| | #2 | 1.04 | -0.16 | | |
| | | 1.21 | 0.01 | | |
| | | 1.18 | -0.02 | | |
| FEBRUARY 14 | #1 | 1.12 | -0.06 | 1.09 | -0.09 |
| | | 1.04 | -0.14 | | |
| | | 1.07 | -0.11 | | |
| | #2 | 1.12 | -0.06 | | |
| | | 1.06 | -0.12 | | |
| | | 1.12 | -0.06 | | |
| FEBRUARY 21 | #1 | 0.92 | -0.21 | 0.97 | -0.16 |
| | | 0.92 | -0.21 | | |
| | | 1.02 | -0.11 | | |
| | #2 | 0.94 | -0.19 | | |
| | | 0.92 | -0.21 | | |
| | | 1.08 | -0.05 | | |
| FEBRUARY 28 | #1 | 1.04 | -0.10 | 1.05 | -0.09 |
| | | 1.08 | -0.06 | | |
| | | 1.02 | -0.12 | | |
| | #2 | 1.09 | -0.05 | | |
| | | 1.05 | -0.09 | | |
| | | 1.00 | -0.14 | | |
| MARCH 7 | #1 | 0.95 | -0.16 | 1.05 | -0.06 |
| | | 1.13 | 0.02 | | |
| | | 1.09 | -0.02 | | |
| | #2 | 0.94 | -0.17 | | |
| | | 1.09 | -0.02 | | |
| | | 1.10 | -0.01 | | |
| MARCH 14 | #1 | 0.91 | -0.23 | 1.00 | -0.14 |
| | | 1.00 | -0.14 | | |
| | | 1.07 | -0.07 | | |
| | #2 | 0.95 | -0.19 | | |
| | | 1.02 | -0.12 | | |
| | | 1.06 | -0.08 | | |

FIG. 7

CALCIUM ION CONCENTRATION MEASURING DEVICE

FIELD OF THE ART

This invention relates to a calcium ion concentration measuring device that measures a concentration of a calcium ion contained in blood.

BACKGROUND ART

Since a concentration of a calcium ion contained in blood is relatively low, in order to measure the concentration of the calcium ion using a conventional calcium ion concentration measuring device as shown in the patent document 1, it is necessary to transport the blood collected from domestic animal to a laboratory and to keep a temperature of the collected blood at constant. In addition, a stationary type measuring device installed in a laboratory where a room temperature is kept constant is used to measure the concentration of the calcium ion.

However, such conventional measurements require facilities to control the temperature of the sample and the room temperature, and also need to measure the concentration of the calcium ion after the blood is transported to the laboratory and the blood temperature becomes stable, resulting in a problem of taking a long time to conduct the measurement.

A device can also be conceived that measures the concentration of the calcium ion in the blood at a site where the blood is collected without transporting the blood to the laboratory, however, if a temperature control device is incorporated in order to maintain a constant blood temperature and a measurement temperature of the blood of a domestic animal, it is likely to be bulky and costly to measure.

PRIOR ART DOCUMENTS

Patent Document

PATENT DOCUMENT 1 Japanese Unexamined Patent Application Publication No. 2007-024544

DISCLOSURE OF THE INVENTION

Problems to be Solved by the Invention

The present claimed invention is made in view of the above-mentioned problems, and an object of this invention is to provide a calcium ion concentration measuring device that can measure a concentration of a calcium ion in blood of a domestic animal with high accuracy without being affected by a temperature on the spot where the blood is collected.

Means to Solve the Problems

More specifically, a calcium ion concentration measuring device in accordance with the present claimed invention is to measure a concentration of a calcium ion in blood of a domestic animal, and comprises a responsive membrane that selectively reacts to the calcium ion, an internal liquid housed in a space separated from the outside by the responsive membrane and an internal electrode arranged to be in contact with the internal liquid, and is characterized by that an isothermal intersection point of the internal liquid is set within a range of the concentration of the calcium ion contained in the blood of the domestic animal.

In accordance with the calcium ion concentration measuring device having the above-mentioned arrangement, since the isothermal intersection point of the internal liquid is set within the range of the concentration of the calcium ion contained in the blood of the domestic animal, it is possible to minimize the influence of the temperature due to the body temperature of the domestic animal or the air temperature (ambient temperature, ambient environment).

As a result of this, the measurement result is difficult to be affected by the temperature, and the calcium ion concentration in the blood of the domestic animal can be accurately measured immediately on the spot where the blood is collected.

In addition, since there is no need of devices or facilities to keep the temperature of the blood and the measurement temperature constant, it is possible to suppress the measurement cost low.

As a concrete embodiment of the present claimed invention represented is that the isothermal intersection point is 0.1 mM or more and 20 mM or less.

If the calcium ion concentration measuring device is provided with a lid body covering the responsive membrane, in spite of a case of measuring the calcium ion concentration outdoors, it is possible to be difficult to be affected by the ultraviolet light and to measure the calcium ion concentration in the blood of the domestic animal with higher accuracy.

If a portable calcium ion concentration measuring kit comprises the above-mentioned portable calcium ion concentration measuring device, a calibration solution and a washing solution, since the calibration solution and the washing solution necessary for measurement of the calcium ion concentration are previously prepared, it is possible to conduct the measurement on a spot where the calcium ion concentration in the blood of the domestic animal is collected.

If the portable calcium ion concentration measuring kit has an ionic strength of the calibration solution that is set within a range of the ionic strength of the blood of the domestic animal, it is possible to make the ionic strength of the calibration solution close to the ionic strength in the blood of the domestic animal so that the concentration of the calcium ion in the blood can be measured with high accuracy by suppressing the influence of the ionic strength on the measurement result.

If the portable calcium ion concentration measuring kit has the washing solution that contains a proteolytic enzyme, it is possible to suppress attachment of protein to the responsive membrane or liquid junction of the calcium ion concentration measuring device.

Effect of the Invention

Since the isothermal intersection point of the internal liquid is set within the range of the concentration of the calcium ion in the blood of the domestic animal, it is possible to minimize the influence of temperature such as body temperature of the domestic animal or air temperature. As a result of this, it is possible to make the measurement result less susceptible to the temperature and to measure the concentration of the calcium ion in the blood of the domestic animal with high accuracy on the spot where the blood sample is collected.

Since the concentration of the calcium ion in the blood of the domestic animal can be measured immediately after the blood is collected, it is possible to conduct a treatment quickly on the domestic animal suspected of having hypocalcemia due to low calcium ion concentration in blood.

BRIEF DESCRIPTION OF THE DRAWINGS

FIG. 6 is a table showing a result of measuring the calcium ion concentration in accordance with one embodiment of this invention.

FIG. 7 is a table showing a result of measuring the calcium ion concentration in accordance with a first example of this invention.

LIST OF REFERENCE CHARACTERS

Figure 1:
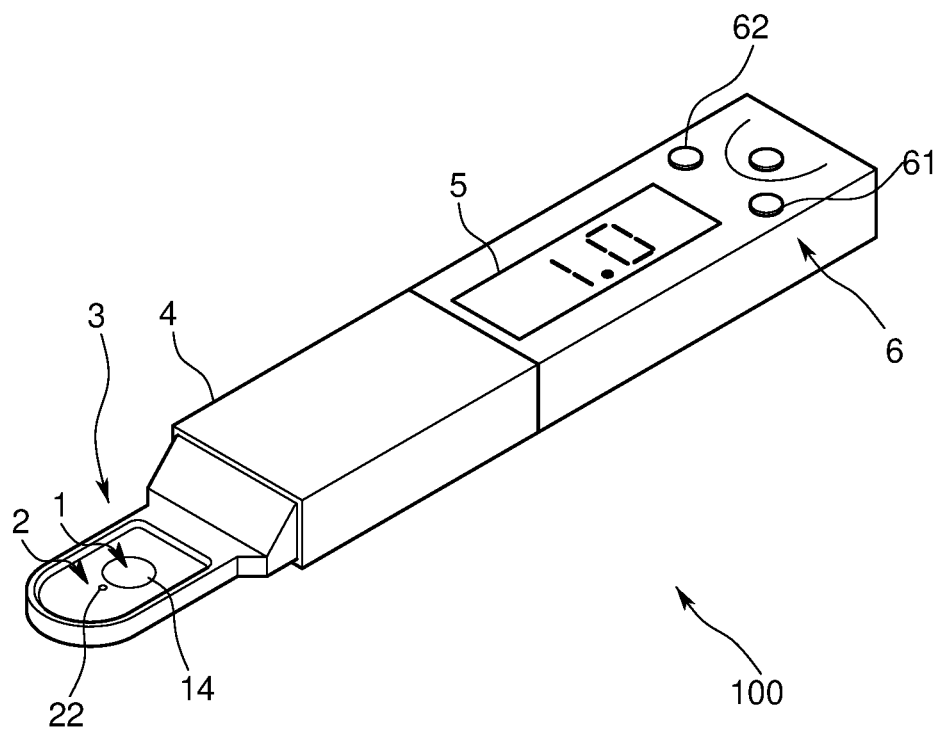
FIG. 1 is an overall schematic view of a portable calcium ion concentration measuring device in accordance with one embodiment of this invention.

100 . . . calcium ion concentration measuring device
12 . . . internal electrode
13 . . . internal liquid
14 . . . responsive membrane
200 . . . calcium ion concentration measuring kit
L, H . . . calibration solution
W . . . washing solution Best Modes of Embodying the Invention A calcium ion concentration measuring device 100 in accordance with one embodiment of the present claimed invention will be explained with reference to drawings.

For example, in rearing dairy cows, an advancing calcium deficiency may cause various diseases, which may seriously affect milk production, breeding or the like.

Then, it is necessary to periodically measure a concentration of calcium ions contained in blood, and to administer calcium supplements to individuals whose concentration of the calcium ion in the blood is lower than a predetermined value.

Such health management is important not only for dairy cows but also for various domestic animals including livestock or pets such as cattle, horses, pigs, goats, sheep, chickens, dogs, cats, hamsters, parakeets or the like.

The calcium ion concentration measuring device 100 in accordance with this embodiment is a portable calcium ion concentration measuring device 100 in order to measure the concentration of the calcium ions in the blood of the domestic animal that can accurately measure the concentration of the calcium ion in the blood on the spot where the blood is collected for health management of the domestic animal.

<Configuration of the Calcium Ion Concentration Measuring Device in Accordance with this Embodiment>

The calcium ion concentration measuring device 100 is a portable device that can be carried around and used as shown in FIG. 1.

The calcium ion concentration measuring device 100 is a composite type with a measuring electrode 1 as being an ion selective electrode integrated with a reference electrode 2, and comprises a sensor part 3 that detects calcium ions in a sample by making contact with the sample, a calculation part that calculates the concentration of the calcium ions detected by the sensor part 3 and a casing 4 that houses the sensor part 3 and the calculation part.

The casing 4 is shaped like an elongated cylinder that is thick enough to be held by a user with one hand, and the entire length is large enough to fit in the palm of the hand.

The casing 4 is provided with a display part 5 that displays the calcium ion concentration calculated by the calculation part and a status of the calcium ion concentration measuring device 100 and an operation part 6 comprising an operation button to operate the calcium ion concentration measuring device 100.

The calculation part is so configured that, for example, an information processing circuit equipped with a CPU, a memory, an A/D converter, a D/A converter, and the like performs its function by the cooperation of the CPU and its peripheral devices according to programs stored in a predetermined area of the memory.

The sensor part 3 is a planar sensor on a surface of which provided are the measuring electrode 1 for detecting the calcium ions and the reference electrode 2 for obtaining reference potential.

The measuring electrode 1 comprises a substrate 11, an internal electrode 12 for the measuring electrode formed on the substrate 11, a gelled or liquid internal liquid 13 arranged in contact with the internal electrode 12 for the measuring electrode, and a responsive membrane 14 electrically connected to the internal electrode 12 for the measuring electrode through the internal liquid 13 for the measuring electrode.

The reference electrode 2 comprises an internal electrode 21 for the reference electrode, a liquid junction 22 and an internal liquid 23 for the reference electrode arranged to make contact with both the internal electrode 21 for the reference electrode and the liquid junction 22.

The measuring electrode 1 and the reference electrode 2 will be explained in detail by the use of FIG. 2 and FIG. 3.

Figure 2:
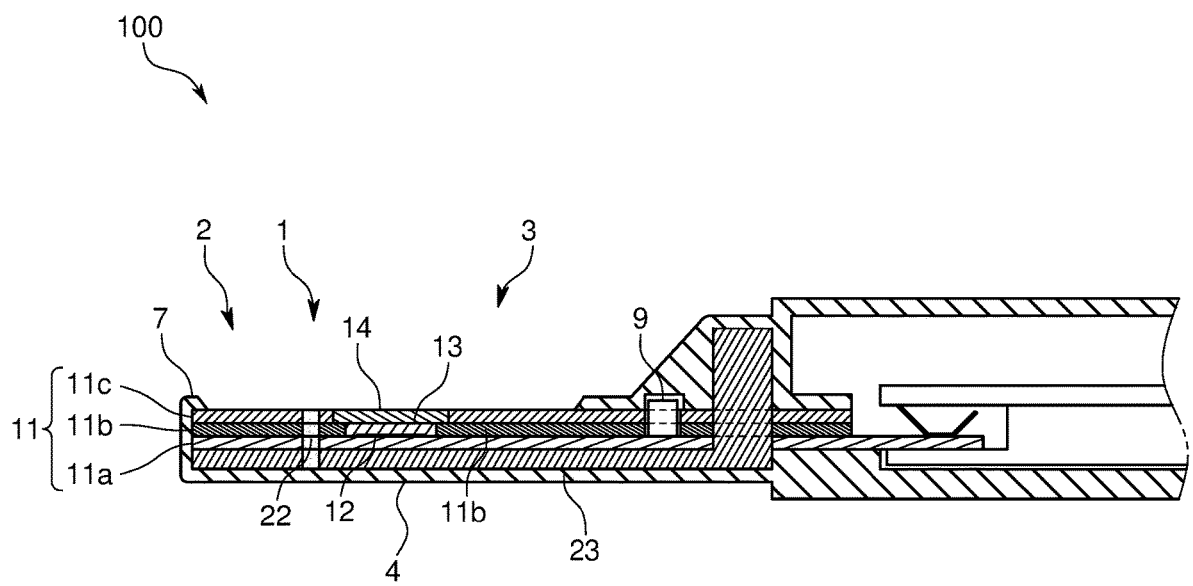
FIG. 2 is a schematic view of a configuration of a sensor part of the portable calcium ion concentration measuring device of this embodiment.
Figure 3:
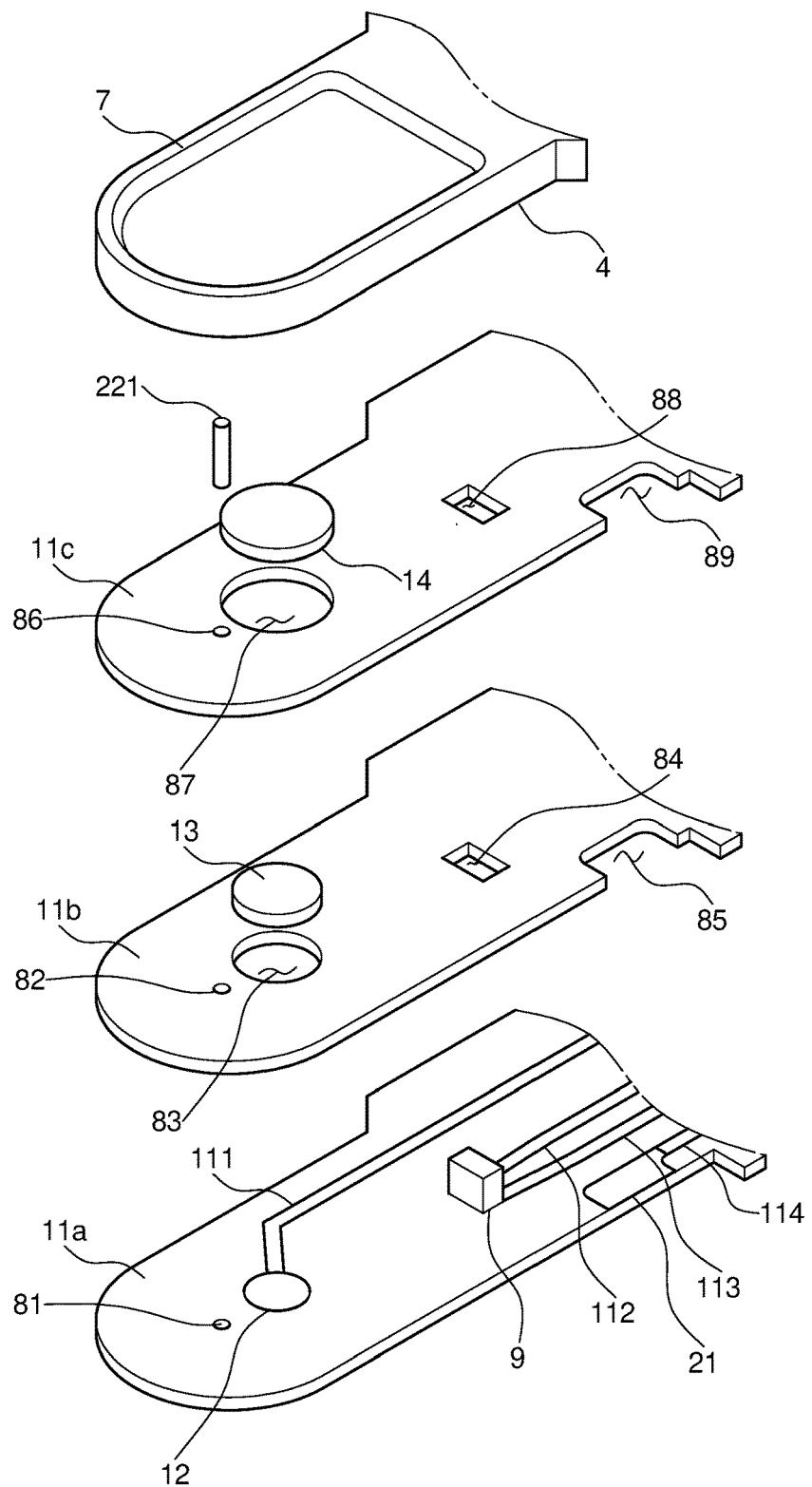
FIG. 3 is a schematic view of a configuration of a sensor part of the portable calcium ion concentration measuring device of this embodiment.

As shown in FIG. 2 and FIG. 3, the sensor part 3 as being the planer sensor comprises mutually laminated three substrates 11a, 11b and 11c made of electrically insulating materials such as polyethylene terephthalate or the like.

A part of each of the substrates 11a, 11b, 11c is formed in an arc with the third substrate 11c as a top layer and the second substrate 2b as a middle layer having the same planar shape (outline), and the first substrate 11a as a lower layer having the same arc-shaped part as that of the substrates 11b and 11c but the opposite side being slightly longer than those of the substrates 11b and 11c. Also, a tested solution holder 7 is arranged to surround the periphery of the third substrate 11c.

Conductive parts 111, 112, 113 and 114 are formed on an upper surface of the first substrate 11a by silk-screening with, for example, an Ag paste after being treated with a predetermined pretreatment and a circular through bore 81 is formed.

The conductive parts 111, 112, 113, 114 are processed as follows. More specifically, a distal end of the conductive part 111 locating at one outside is coated with AgCl to form a circular inner electrode 12 for the measuring electrode, and a distal end of the conductive part 114 locating at the other outside is also coated with AgCl to form an elongated inner electrode 21 for the reference electrode locating at one side end part of the substrate 11a.

A temperature compensation element 9 such as a thermistor is arranged over a distal end of the inner conductive part 112 and a distal end of the inner conductive part 113 locating inside. And the other part of each of the conductive parts 111, 112, 113, 114 constitutes a lead part.

The second substrate 11b is provided with a through bore 82 that has the same diameter as that of the through bore 81 and that is formed at a position corresponding to the through bore 81, a through bore 83 that has a slightly larger diameter than that of the inner electrode 12 for the measuring electrode and that is the formed at a position corresponding to the inner electrode 12 for the measuring electrode, and a rectangular through bore 84 that has approximately the same size as that of the temperature compensation element 9 and that is formed in a position corresponding to the temperature compensation element 9. Furthermore, an elongated notch 85 is formed at a side end part corresponding to the inner electrode 21 for the reference electrode.

The third substrate 11c is provided with a through bore 86 that has the same diameter as that of the through bores 81, 82 and that is formed at a position corresponding to the through bores 81 and 82, a through bore 87 that has a slightly larger diameter than that of the through bore 83 and that is arranged at a position corresponding to the through bore 83, and a through bore 88 that has the same diameter as that of the through bore 84 and that is arranged at a position corresponding to the through bore 84. Furthermore, a notch 89 having the same size as that of the notch 85 is formed at a position corresponding to the notch 85.

A liquid junction 22 of the reference electrode 2 comprising a porous body 221 made of polyethylene is loaded to the through bores 81, 82 and 86 arranged at a respectively corresponding position on each of the substrates 11a, 11b and 11c so as to pass the through bores 81, 82, 86. The liquid junction 22 is loaded in such a way that the liquid junction 22 is nearly flush with the upper surface of the third substrate 11c as being the third layer.

The gelled internal liquid 13 for the measuring electrode is loaded to the through bore 83 formed on the second substrate 11b.

The gelled internal liquid 13 is formed in a shape of a disk by applying an agar as a gelling agent and glycerin as a gel evaporation inhibitor to the internal liquid made by adding calcium ions to a pH buffer solution containing, for example, KCl. The concentration of a chloride ion of the internal liquid is adjusted to 3.3 M.

The gelled internal liquid 13 is loaded to the through bore 83 with its upper surface slightly protruding above the upper surface of the second substrate 11b. The internal liquid 13 is in contact with the internal electrode 12 for the measuring electrode formed on the upper surface of the first substrate 11a through the through bore 83.

A calcium ion responsive membrane 14 formed in a shape of a disk is loaded to the through bore 87 formed on the third substrate 11c. The responsive membrane 14 is in contact with the gelled internal liquid 13 and is fixed so as to be nearly flush with the upper surface of the third substrate 11c.

The calcium ion responsive membrane 14 is a semipermeable solid formed by adding plasticizer and calcium ionophore to polyvinyl chloride (PVC), by filling a material dissolved in an organic solvent such as tetrahydrofuran (THF) into the through bore 87 by potting, ink-jet printing, or the like, and then by applying heat so as to evaporate an organic solvent.

The gelled internal liquid 23 for the reference electrode is provided in the casing 4 across an area from the below of the bottom layer of the first substrate 11a to the above of the top layer of the third substrate 11c.

The gelled internal liquid 23 for the reference electrode is filled in a space between a side part of the inner electrode 21 side of the reference electrode 2 and the casing 4 so as to be in communication with the substrates 11a, 11b and 11c, and the upper and lower parts of the internal liquid 23 are in contact with the surface of the internal electrode 21 for the reference electrode and the lower end part of the liquid junction 22.

The gelled internal liquid 23 for the reference electrode is formed by applying an agar as a gelling agent and glycerin as the gel evaporation inhibitor to the internal liquid made by adding calcium ions to the pH buffer containing KCl.

Then, both the gelled internal liquid 13 for the measuring electrode and the gelled internal liquid 23 for the reference electrode are made so that the isothermal intersection point for the calcium ion concentration is contained within a range of the calcium ion concentration in the blood of the domestic animal.

The isothermal intersection point in this embodiment is an ionic activity (an ionic concentration) of an ion to be measured in the internal liquid of the measuring electrode 1 and the reference electrode 2 at a time when there is no change in a membrane potential of the responsive membrane 14, even though the measurement temperature changes.

Since the concentration of calcium ions in the blood of the domestic animal is 0.1 mM or more and 20.0 mM or less, in this embodiment, each of the calcium ion concentrations of the internal liquid 13 for the measuring electrode and the internal liquid 23 for the reference electrode is set at 1.0 mM.

In addition, an amount of calcium chloride and an amount of potassium chloride added to the internal liquid 13 for the measuring electrode and the internal liquid 23 for the reference electrode are adjusted so that the chloride ion concentration of the internal liquid 13 for the measuring electrode and the internal liquid 23 for the reference electrode is 3.3 M.

For the calcium ion concentration measuring device 100 of this embodiment, the measurement range is set to be 0.1 mM or more and 5.0 mM or less.

<Configuration of the Calcium Ion Concentration Measuring Kit in Accordance with this Embodiment>

Figure 4:
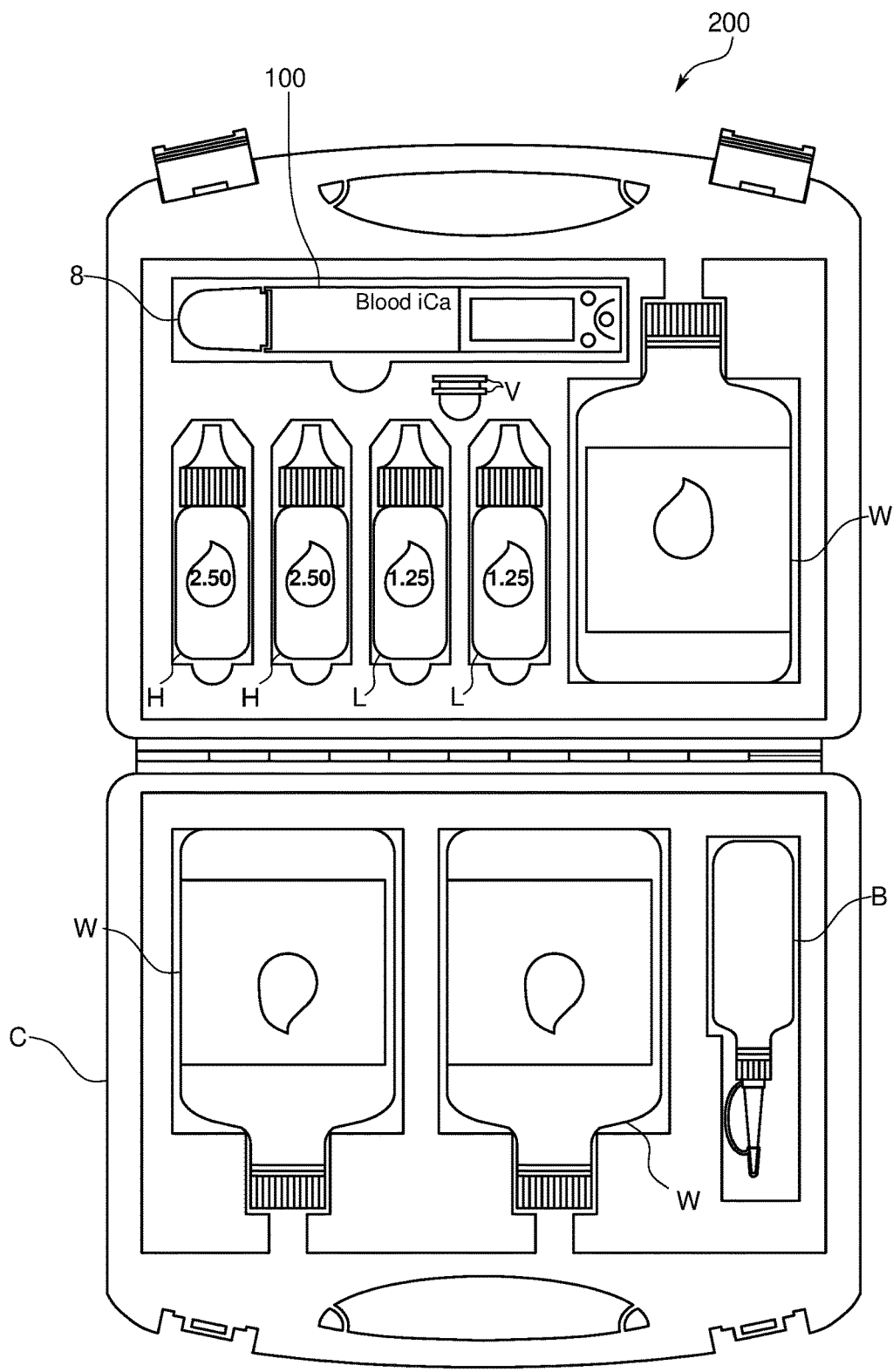
FIG. 4 is a schematic view of a portable calcium ion concentration measuring kit in accordance with this embodiment.

In this embodiment, as shown in FIG. 4, it is so configured that a calcium ion concentration measuring kit 200 consists of the above-mentioned portable calcium ion concentration measuring device 100, calibration solutions (L) and (H) used to calibrate the calcium ion concentration measuring device 100, a washing solution (W) to clean the sensor part 3, and a carrying case (C) to house and carry the above items.

Each of the constituting elements of this calcium ion concentration measuring kit 200 will be explained below except for the calcium ion concentration measuring device 100.

The calibration solutions (L) and (H) contain calcium ions, sodium ions and potassium ions, and the ionic strength is set within the range of the ionic strength of the blood of the domestic animal.

Concretely, the ionic strength of the calibration solution (L) and the ionic strength of the calibration solution (H) are set to be approximately 0.090 or more and 0.160 or less.

Two types of the calibration solutions (L) and (H) are prepared, and the calcium ion concentrations of the two calibration solutions (L) and (H) are set to differ from each other.

The calibration solution having the lower calcium ion concentration (low concentration calibration solution (L)) contains, for example, a buffer solution whose pH is adjusted to neutral, calcium chloride, sodium chloride, potassium chloride or the like, and the calcium ion concentration of the calibration solution (L) is set to be, for example, 1.20 mM or more and 1.30 mM or less.

Other ion concentration contained in the low concentration calibration solution (L) is set so that, for example, the sodium ion is 130.00 mM or more and 170.00 mM or less, the potassium ion is 4.00 mM or more and 6.00 mM or less, and the pH is 7.20 or more and 7.50 or less.

In addition, the ionic strength of the low concentration calibration solution (L) is set to be, for example, 0.14 or more and 0.16 or less.

The calibration solution having the higher calcium ion concentration (high concentration calibration solution (H)) contains, for example, a buffer solution whose pH is adjusted to neutral, calcium chloride, sodium chloride, potassium chloride or the like, and the calcium ion concentration of the calibration solution (H) is set to be, for example, 2.45 mM or the more and 2.55 mM or less.

Other ion concentration contained in the high concentration calibration solution (H) is set so that, for example, the sodium ion is 80.00 mM or more and 120.00 mM or less, the potassium ion is 1.70 mM or more and 1.90 mM or less, and the pH is 6.70 or more and 7.00 or less. In addition, the ionic strength of the high concentration calibration solution (H) is set to be, for example, 0.090 or more and 0.11 or less.

Both of the two calibration solutions (L) and (H) are designed to be stored at 5° C. to 30° C. for about 30 months after manufacture.

The washing solution (W) prevents contaminants resulting from the blood as being the sample from adhering to the sensor part 3 of the calcium ion concentration measuring device 100, and the washing solution (W) contains a proteolytic enzyme.

In addition, a composition of the washing solution (W) does not contain a surfactant agent that may adversely affect the performance of the responsive membrane 14.

The washing solution (W) contains a buffer solution whose pH is adjusted to neutral, a salt having a high concentration to hemolyze blood cells and a preservative to inhibit microbial growth.

The buffer solution is not particularly limited as long as it is a neutral buffer such as a tris buffer solution or a phosphate buffer solution of 0.5% by weight or more and 1.0% by weight or less.

The salt may be any as long as it can improve the concentration of salt in the washing solution (W) to a range between 0.5% by weight or more and 1.0% by weight or less where blood cells are hemolyzed, and various salts such as natrium chloride, potassium chloride, sodium sulfate, potassium sulfate or the like may be appropriately used.

The amount of the proteolytic enzyme to be added may be in a range of, for example, 0.5% by weight or more and 1.0% by weight or less.

The preservative is not particularly limited, however, the preservative is preferably capable of suppressing the growth of microorganisms to an extent that there is no problem with use even after storing the washing solution for about 20 months at 5° C. to 30° C.

In addition to the above-mentioned portable calcium ion concentration measuring device 100, the calibration solutions (L), (H) and the washing solution (W), the carrying case (C) houses a battery (V), a washing bottle (B) for washing solution and an instruction manual in its inside, and a handle is provided so that it can be carried easily with one hand.

<Method for Measuring the Concentration of Calcium Ions in Blood in Accordance with this Embodiment>

Figure 5:
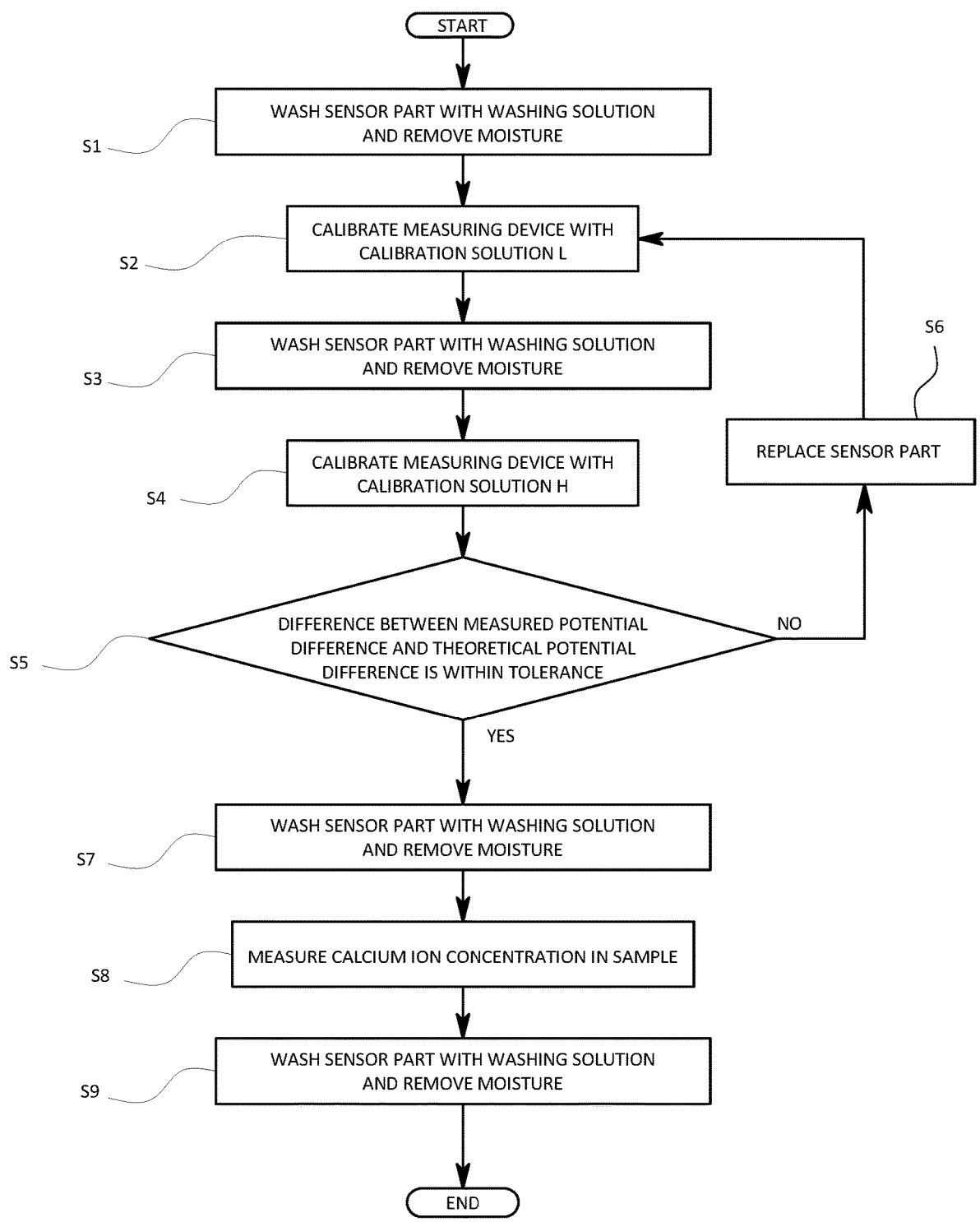
FIG. 5 is a flow chart showing a method for measuring a concentration of a calcium ion using the portable calcium ion concentration measuring kit in accordance with this embodiment.

A method for measuring calcium ion concentration in blood of a domestic animal using the above-mentioned portable calcium ion concentration measuring kit 200 will be explained with reference to FIG. 5.

First, take the calcium ion concentration measuring kit 200 to a farm where the domestic animal is raised and turn on the calcium ion concentration measuring device 100.

To prepare for the measurement, first clean the sensor part 3 of the calcium ion concentration measuring device 100 with the washing solution (S1).

Next, calibrate the calcium ion concentration measuring device 100 by the use of the calibration solutions (L) and (H). In this embodiment, the device 100 is calibrated at two points.

In order to start the calibration, first, press a calibration button 61 arranged in an operation part 6.

When the calibration button 61 is pressed, an instruction is displayed on a display part 5 to drop the low concentration calibration solution (L) into the sensor part 3. In accordance with this instruction, the user covers the liquid junction 22 and the responsive membrane 14 of the sensor part 3 and applies a drop of the low concentration calibration solution (L) to the test solution holder by an amount of a degree that the low concentration calibration solution (L) does not overflow, and then press the calibration button 61 (S2). After the display part 5 shows that the first calibration is completed, the sensor part 3 is washed once with the washing solution (W), and moisture is removed from the sensor part 3 with a tissue or the like (S3).

Note that after calibration is completed, here, it is between the calibration and the calibration.

Next, an instruction is displayed on the display part 5 to drop the high concentration calibration solution (H) into the sensor part 3. In accordance with this instruction, the user covers the liquid junction 22 and the responsive membrane 14 of the sensor part 3 and applies a drop of the high concentration calibration solution (H) to the test solution holder by an amount of a degree that the high concentration calibration solution (H) does not overflow, and then press the calibration button 61 (S4).

If a difference of the potential difference measured at the two points from the theoretical potential difference calculated based on the difference between the concentration of the calcium ions in the calibration solution (L) and that in the calibration solution (H) exceeds a predetermined threshold, a warning is displayed on the display part 5 to notify the user that it is time to replace the sensor part 3 (S5). If the warning that notifies the user that it is time to replace the sensor part 3 is displayed, the sensor part 3 is replaced (S6), and then the two-point calibration is performed again.

It is possible to set the above-mentioned difference relative to an absolute value of the difference between a percentage representing the measured potential difference between the two points and a percentage representing the theoretical potential difference between the two points when a ratio of the measured potential difference between the two points to the theoretical potential difference between the two points is expressed as a percentage, and the above-mentioned threshold is set to be ±20% in this embodiment.

On the other hand, in case that the above-mentioned difference is less than or equal to the predetermined threshold and the calibration is completed without any problem, the indication that the calibration is completed is displayed on the display part 5 (S5). Note that the calibration is completed is the time between the calibration and the measurement.

In this case, the sensor part 3 is washed with the washing solution (W) and moisture is removed from the sensor part 3 by wiping the sensor part 3 with a tissue (S7), and then the concentration of the calcium ion in the sample is measured (S8). The washing may be performed not only between the measurements, but also between the measurement and the next calibration.

For example, whole blood of a bovine collected by a veterinarian is used as the sample. If the whole blood of the bovine is used as it is for the measurement, the blood coagulates during the measurement, so an anticoagulant such as lithium heparin is added to the collected whole blood immediately on the spot where the blood is collected. Concretely, the collected blood of domestic animals may be added to a blood collection container into which the anticoagulant containing lithium heparin is previously put and be mixed.

The whole blood of the bovine to which the anticoagulant is added is dripped on the sensor part 3 so as to cover the liquid junction 22 and the responsive membrane 14 of the sensor part 3 on the spot where the blood is collected. When the measurement button 62 arranged in the operation part 6 is pushed to start the measurement, the measurement is started. When the measurement value becomes stable, both the fact that the measurement is started and the calcium ion concentration are displayed on the display part 5, and then the calcium ion concentration measurement is completed. At this time, the calcium ion concentration is to be displayed to one decimal place.

The calcium ion concentration displayed on the display part 5 can be displayed by rounding down decimal places or to two decimal places depending on the purpose, and the display format can be freely changed by the user by operating the button on the operation part 6.

After the measurement of one sample is completed, the sensor part 3 is washed with washing solution (W), and moist is removed from the sensor part 3 (S9), and then the next sample is measured.

Effect of this Embodiment

In accordance with the portable calcium ion concentration measuring device 100 and the kit 200 having the above arrangement, the following effects can be achieved.

Since the isothermal intersection point of the internal liquid 13 for the measuring electrode and the internal liquid 23 for the reference electrode is set within the range of the calcium ion concentration in the blood of the domestic animal, the influence of the temperature on the measured values can be suppressed. As a result of this, the measured value is less susceptible to the temperature of the sample due to the body temperature of the domestic animal and the air temperature so that the calcium ion concentration in the blood can be measured accurately on the spot where the blood sample is collected.

Since there is no need of measuring the calcium ion concentration while controlling the temperature of the sample, it is not necessary to transport the collected sample or to use expensive measurement equipment that can control the temperature, resulting in reducing the cost of the measurement to less than one-third of conventional methods.

Since the size of the calcium ion concentration measuring device 100 is such that it fits in the palm of the user's hand and the sensor part 3 is a liquid film type flat sensor, it is possible to reduce the amount of the sample required for measurement.

In addition, since the calcium ion concentration measuring device 100 has a test liquid holder 7 arranged to surround the sensor part 3, there is no need of separately preparing a container to hold the blood sample.

As indicated by the numerical code 8 in FIG. 4, although omitted in FIG. 2 and FIG. 3, since a lid body 8 covering the sensor part 3 is provided, an influence from the UV light can be reduced in case of measuring the calcium ion concentration especially in outdoor so that it is possible to conduct a more accurate measurement of the calcium ion concentration in the blood of the domestic animal.

Since the calcium ion concentration measuring kit 200 is equipped with the calcium ion concentration measuring device 100, the calibration solutions (L) and (H), the washing solution (W) and the carrying case (C) that houses the device 100, the solutions (L) and (H) and the solution (W), it is possible to eliminate the labor of preparing the calibration solutions (L) and (H) and the washing solution (W) in advance.

In addition, since the calibration solutions (L) and (H) and the washing solution (W) can be stored at 5° C.~30° C., it is also possible to store them while put in the carrying case (C) together with the calcium ion concentration measuring device 100.

Since the calcium ion concentration measuring device 100, calibration solutions (L) and (H), and the washing solution (W) can be stored in the carrying case (C) and transported to a stable where the domestic animal is kept or to an open-air pasture, it is possible to conduct the measurement of the calcium ion concentration in the blood immediately on the spot where the blood is collected from the domestic animal.

Since the ionic strength of the calibration solutions (L) and (H) is set within the range of the ionic strength of the blood of the domestic animal, it is possible to calibrate the calcium ion concentration measuring device 100 with high accuracy.

Since the washing solution (W) contains the salt, it is possible to break and hemolyze the blood cells in the blood of the domestic animal by the osmotic pressure. In addition, since the washing solution (W) further contains a proteolytic enzyme, it is possible to break down the proteins in the blood. As a result of this, the viscosity of the blood can be lowered and adhesion of dirt by the blood to the sensor part 3 can be suppressed.

In addition, since the sensor part 3 is washed with the washing solution (W) after the completion of the calibration or the completion of the measurement every time the sensor part 3 comes in touch with the calibration solution or the sample, it is possible to make the sensor part 3 less likely to be contaminated and to extend the life of the sensor part 3 more than when the sensor part 3 is washed with water or the like without washing the sensor part 3 every time with the washing solution (W).

Since a guide display is displayed on the display part 5 to perform the two-point calibration if the calibration button 61 is pressed, it is possible for any user who is not familiar with using the kit 200 to calibrate the calcium ion concentration measuring device 100 accurately and easily.

Since lithium heparin does not affect the concentration of electrolytes in the blood if the lithium heparin is used as the anticoagulant, it is possible to measure the calcium ions concentration in the blood more accurately.

Other Embodiments of the Invention

The present claimed invention is not limited to the above-mentioned embodiments.

The isothermal intersection point of the above-mentioned internal liquid to the calcium ions may be 0.1 mM to 2.0 mM, 0.1 mM to 10 mM, 0.1 mM to 5 mM, 0.1 mM to 4 mM, 0.5 mM to 5 mM, and more preferably 0.5 mM to 2 mM.

The isothermal intersection point varies depending on the ionic activity of the ions to be measured and the ionic activity of chloride ions in the internal liquid of the measuring electrode and the internal liquid of the reference electrode. Then, in addition to keeping the calcium ion concentration of the internal liquid within a range of the calcium ion concentration in the blood of the domestic animal, the isothermal intersection point may also be adjusted to be contained within a range of the calcium ion concentration in the blood of the domestic animal by adjusting the above-mentioned ion activity.

The calcium ion concentration contained in the low concentration calibration solution may be 0.50 mM to 1.5 mM, 1.00 mM to 1.50 mM, and is more preferably 1.20 mM to 1.30 mM. The calcium ion concentration contained in the high concentration calibration solution may be 2.00 mM to 6.00 mM, 2.50 mM to 5.00 mM, and is more preferably 2.45 mM to 2.55 mM.

In addition, the sodium ions, the potassium ions and pH other than the calcium ions contained in the low concentration and high concentration calibration solutions can be appropriately changed as long as the ionic strength as a whole of each calibration solution is within the range of the ionic strength of the blood of the domestic animal.

Concretely, for example, the concentration of the sodium ions contained in the low concentration calibration solution may be 0.01 mM to 200 mM, 0.01 mM to 170.00 mM, and is preferably 100.00 mM to 170.00 mM. The potassium ion concentration contained in the low concentration calibration solution may be 0.01 mM to 150 mM, 4.00 mM to 140 mM, and is more preferably 4.00 mM to 6.00 mM.

The concentration of the sodium ions contained in the high concentration calibration solution may be 0.01 mM to 300 mM, 0.01 mM to 250.00 mM, and is more preferably 80.00 mM to 120.00 mM. The concentration of the potassium ions contained in the high concentration calibration solution may be 0.01 mM to 150 mM, 1.00 mM to 131 mM, and is more preferably 1.60 mM to 2.00 mM.

In addition, in order to make the calibration solutions (L) and (H) more similar to the composition of the blood of the domestic animal, the calibration solutions (L) and (H) may contain, for example, magnesium ions, chloride ions, hydrogen carbonate ions, hydrogen phosphate ions, sulfate ions or the like, in addition to the above-mentioned ions.

The content of each of these ions may be set as follows in accordance with the composition of the blood of the domestic animal.

The magnesium ion concentration may be, for example, about one hundredth of the sodium ion concentration.

For negatively charged ions such as chloride ions, hydrogen carbonate ions, hydrogen phosphate ions, sulfate ions or the like, if the total number of negatively charged ions is 100, for example, the chloride ion concentration may be 78.5, the hydrogen carbonate ion concentration may be 16.7, the hydrogen phosphate ion concentration may be 2.4, and the sulfate ion concentration may be about 2.4.

The ion intensities of the low and high concentration calibration solutions containing these ions may be within a range of the ion intensities of the blood of the domestic animal, and may be 0.010 to 0.500, 0.050 to 0.300, and are more preferably 0.070 to 0.220.

Although the predetermined threshold at a time of warning that it is time to replace the sensor was set at 20% in the above-mentioned embodiment, this threshold may be in a range of, for example, 5% to 30%, and may be selected appropriately depending on the purpose of the measurement. In addition, it is not limited to the measured potential difference between two points and the theoretical potential difference between two points expressed as the percentage, but the threshold may be provided for the difference between these potential differences.

The calcium ion concentration measuring device is not limited to a planar sensor type, but may also be used by immersing the sensor part arranged to protrude from a distal end part of the casing 4 in the sample.

The calibration may be performed not only as the two-point calibration as described above, but also as a three-point calibration or as a one-point calibration.

The portable calcium ion concentration measuring kit may be provided with a blood collection container inside of which an anticoagulant containing lithium heparin is previously put. In addition, various modifications and combinations of embodiments may be made without departing from a spirit of the invention.

EXAMPLE

The present claimed invention will be described in more detail by way of examples, but the present claimed invention is not limited to these examples.

Example 1

The following experiments were conducted to investigate the effect of the temperature change on the measurement results by the use of the calcium ion concentration measuring device and the calcium ion concentration measuring kit explained in detail in the above-mentioned embodiments. A concrete experimental procedure is as follows.

The blood from a human being collected in a heparin-lithium blood collection tube was used as the sample.

The samples taken from the same blood collection tube were brought to 5° C., 25° C. and 37° C. in thermostatic chambers respectively, and the room temperature at which the samples at each temperature were measured was also kept at 5° C., 25° C. and 37° C. respectively, according to the temperature of the samples.

The calcium ion concentration is measured by conducting the two-point calibration on the calcium ion concentration measuring device at the above-mentioned room temperatures respectively by the use of the calibration solution provided in the calcium ion concentration measuring kit, and then by dropping the sample into the sensor part of the calcium ion concentration measuring device by an amount of 195 □L.

The calcium ion concentration of the samples was measured under exactly the same conditions except that the isothermal intersection point of the internal liquid was set at 50 mM, which was outside the range of the calcium ion concentration in the blood of the domestic animal, as a comparison example.

Furthermore, the same samples used in these examples and the comparison examples were subjected to a blood gas measuring device (ABL800FLEX) made by RADIOMETER and the calcium ion concentration in the samples was precisely analyzed.

A table in FIG. 6 indicates comparison of these results. The numerical values in the table are the average values of the three measurements.

According to the results of this table, it can be seen that the change of the measurement is small when the temperature is changed in the example using the calcium ion concentration measuring device of the present claimed invention compared with a case of using a conventional calcium ion concentration measuring device. Especially, the difference in the measurement result was small in this example 1, while the difference between the measurement result in the comparison example and the measurement result by the blood gas measuring device ABL800FLEX was large at a time of the measurement at 5° C.

In addition, it also turns out that the time required to stabilize the measurement at 25° C. and 37° C. was shorter than the time required in the comparison example.

From the above results, in accordance with the calcium ion concentration measuring device of the present claimed invention, it was found that it was possible to minimize the influence of the temperature change on the measurement results.

Example 2

Next, with the cooperation of Kyoto Prefectural Agriculture, Forestry and Fisheries Technology Center, Livestock Technology Department, we examined the calcium ion concentration measuring device and the kit described in the above-mentioned embodiment to see whether or not there was any problem with the accuracy of the calcium ion concentration measurement. The blood samples were collected continuously from the same dairy cows at a rate of approximately once a week.

The measurement of the calcium ion concentration in the blood collected as described above was performed in the same manner as in the example 1, except that the temperature was set to 25° C. for all blood samples. The results are shown in the table in FIG. 7 and the graph in FIG. 8. Explanatory note triangles in the graph in FIG. 8 show the results of measurements using the calcium ion concentration measuring device of the present invention, and explanatory note squares in the graph in FIG. 8 show the results of the precise analysis in ABL800FLEX.

Figure 8:
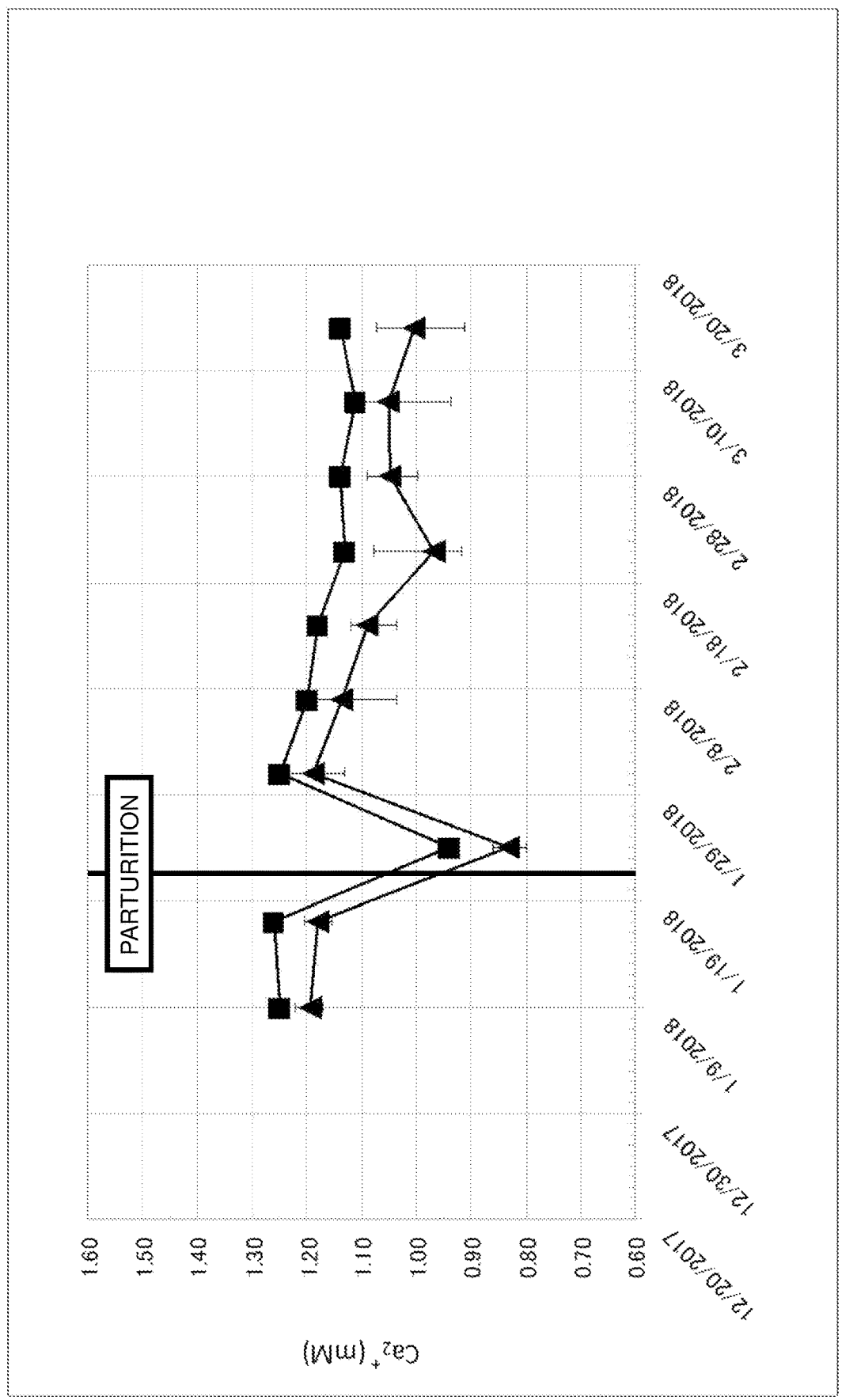
FIG. 8 is a graph showing a result of measuring the calcium ion concentration in accordance with a second example of this invention.

Two calcium ion concentration measuring devices in accordance with this invention were prepared to measure the calcium ion concentration of the same sample, and the measurement was conducted three times by each of the devices and then, the average of six measurements is shown in FIG. 7 and FIG. 8.

According to these results, the measured calcium ion concentration in blood measured by the calcium ion concentration measuring device in accordance with this invention was found to be consistent with the result of the precise analysis by the ABL800FLEX.

As can be seen clearly from the results in FIG. 8, in accordance with the calcium ion concentration measuring device of this invention, it was clearly distinguished that the calcium ion concentration in the blood of the tested dairy cows had decreased immediately after parturition. In addition, it was distinctly discriminated that the calcium ion concentration in the blood had recovered to the same level as that before the parturition by subsequent treatments such as administration of calcium.

These results showed that the calcium ion concentration measuring device of the present claimed invention could be used with good accuracy to screen dairy cows with low blood calcium ion concentrations prior to, for example, a costly thorough examination.

POSSIBLE APPLICATIONS IN INDUSTRY

In accordance with this invention, since the isothermal intersection point of the internal liquid is set within the range of the calcium ion concentration contained in the blood of the domestic animal, it is possible to minimize the influence of temperature on the measured values. As a result of this, the measured value is less susceptible to the temperature of the sample due to the body temperature of the domestic animal and the air temperature so that the calcium ion concentration in the blood can be measured accurately on the spot where the blood sample is collected.

The invention claimed is:

1. A portable calcium ion concentration measuring device that measures a concentration of a calcium ion in blood of a domestic animal, comprising
   a responsive membrane that selectively reacts to the calcium ion,
   an internal liquid housed in a space separated from the outside by the responsive membrane and
   an internal electrode arranged to be in contact with the internal liquid, wherein
   an isothermal intersection point of the internal liquid is set within a range of the concentration of the calcium ion contained in the blood of the domestic animal, and the measurement of the concentration of the calcium ions can be conducted on the spot where the blood of the domestic animal is collected.

2. The portable calcium ion concentration measuring device described in claim 1, wherein
   the isothermal intersection point is 0.1 mM or more and 20 mM or less.

3. The portable calcium ion concentration measuring device described in claim 1, wherein
   the responsive membrane is a semipermeable membrane.

4. The portable calcium ion concentration measuring device described in claim 1, wherein
   the responsive membrane is provided with a lid body covering the responsive membrane.

5. A portable calcium ion concentration measuring kit comprising
   the portable calcium ion concentration measuring device described in claim 1,
   a calibration solution that calibrates the portable calcium ion concentration measuring device, and
   a washing solution that washes the portable calcium ion concentration measuring device.

6. The portable calcium ion concentration measuring kit described in claim 5, wherein
   an ionic strength of the calibration solution is set within a range of the ionic strength of the blood of the domestic animal.

7. The portable calcium ion concentration measuring kit described in claim 5, wherein
   the washing solution contains a proteolytic enzyme.

8. A method for measuring calcium ion concentration that measures a concentration of a calcium ion contained in blood of a domestic animal by the use of a portable calcium ion concentration measuring device comprising a responsive membrane that selectively reacts to the calcium ion, an internal liquid housed in a space separated from the outside by the responsive membrane and an internal electrode arranged to be in contact with the internal liquid, wherein an isothermal intersection point of the internal liquid is set within a range of the concentration of the calcium ion contained in the blood of the domestic animal.

9. The method for measuring calcium ion concentration described in claim 8, wherein the concentration of the calcium ion in the blood of the domestic animal is measured on the spot where the blood is collected.

10. The method for measuring calcium ion concentration described in claim 8, further comprising a washing process wherein the responsive membrane is washed by the use of a washing solution containing a proteolytic enzyme, wherein the washing process is performed after calibrating the portable calcium ion concentration measuring device and after measuring the concentration of the calcium ion contained in the blood of the domestic animal.

* * * * *